United States Patent [19]

Chiu et al.

[11] Patent Number: 5,025,096

[45] Date of Patent: Jun. 18, 1991

[54] PREPARATION OF INDOLE AND INDOLE DERIVATIVES

[75] Inventors: Kuen-Wai Chiu, Mars; Lin-Chen Yu, Allison Park; John R. Strickler, Pittsburgh, all of Pa.

[73] Assignee: Mine Safety Appliances Company, Pittsburgh, Pa.

[21] Appl. No.: 768,461

[22] Filed: Aug. 22, 1985

[51] Int. Cl.$^5$ .................... C07D 491/56; C07D 209/8
[52] U.S. Cl. .................................. 544/234; 544/236; 544/250; 544/280; 544/345; 544/350; 546/83; 546/113; 548/430; 548/508
[58] Field of Search ................ 546/113, 83; 548/508, 548/430; 544/236, 350, 280, 250, 345, 234

[56] References Cited

PUBLICATIONS

W. Houlihan (editor), Heterocyclic Compounds, Indoles, Part One, pp. 394–396 (1972), Wiley-Interscience, N.Y., QD 40114.

R. Lorenz et al., Journal of Organic Chemistry, 30,2531 (1965), A New Indole Synthesis.

*Primary Examiner*—Mary E. Ceperley

[57] ABSTRACT

Indole and indole derivatives are prepared by contacting under mild reaction conditions an N-(2-toly)formidate, N-(3-methyl-2-pyridyl)formimidate, or N-methyldiazyl formimidate with an alkali metal amide.

8 Claims, No Drawings

PREPARATION OF INDOLE AND INDOLE DERIVATIVES

FIELD OF THE INVENTION

The invention relates to a method of preparing indoles and indole deriviatives and more particularly to such method in which a phenyl, pyridyl or diazyl formimidate is reacted with an alkali metal alkylamide.

BACKGROUND OF THE INVENTION

Because of the use of indoles in drug syntheses and in perfumery, the chemistry of the indoles has been investigated very thoroughly. However, the known preparations still do not offer a simple, easy synthesis to this group of chemicals. FOr example, the Fishcer Indole Synthesis, by which a phenylhydraxine of an aldehyde or ketone is heated in the presence of a catalyst such as zinc chloride, boron trifluoride or polyphosphoric acid, is complicated by the synthesis of the phenylhydrazine intermediate which involves tedious N-nitrosation and reduction steps. Furthermore, the reaction fails for indole itself. The Madelung Indole Synthesis, in which formotoluidine is reacted with potassium t-butoxide, is convenient because of the ready accessibility of the starting materials; but the reaction proceeds only at a high reaction temperature (300° C.) and requires the decomposition of half of the intermediate pottassium O-formotoluidide to pottassium toluidide which in turn functions as a strong base to metalate the methyl proton of potassium formotoluidide and effect the cyclization to indole. Because of the aforementioned decomposition reaction mechanism, the reacion gives only a 30–40 percent yield and a lot of tar residue which makes the reaction mixture almost intractable.

Lorenz et al., *J. Org. Chem.*, 30, 2531 (1965) disclose a promising modification of the Madelung synthesis in which N-(2-toly)-N'-methyl-N'-pheynlformamidines are cyclized with sodium N-methylanilide in refluxing N-methylaniline. But this process involves 4 to 5 steps, including a very slow high vacuum distillation of the N-(2-tolyl)-N'-methyl-N'phenylformamidine intermediate and the separation of the product from oil, which make the process industrially unattractive.

The Reissert Indole Syntheses uses O-nitrophenylpyruvic acids as reaction intermediates. Due to the electron withdrawing characteristic of the nitro group, O-nitrophenyl-ptruvis acids are obtainable by condensation of O- nitrotoluenes with diethyloxalate in the presence of a weak base, such as potassium tert-butoxide as catalyst. But the nitro group has to be reduced to amino group prior to the formation of the indole-2-carboxylic acids, which require further decarboxylation at 200°-250° C., to complete the preparation of indoles.

DESCRIPTION OF THE INVENTION

It is an object of this invention to provide a simple and direct method of preparing indoles and indole derivatives. A further object is to provide such a method that proceeds under mild reaction conditions and produces indole or its derivatives in good yield.

In accordance with out invention, an N-(2-tolyl)formimidate derivative, N-(3-methyl-2-pyridyl)formimidate derivative or N-methyldiazyl formimidate derivative is reacted with an alkali metal alkylamide whereby the methyl group is metallates with concurrent cyclization to form an indole nucleus.

Suitable N-(2-tolyl), N-(3-methyl-2-pyridyl), or N-methyldiazyl formimidate derivatives are of the formula

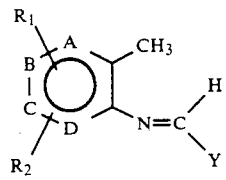

wherein not more than two of A, B, C and D are nitrogen atoms and the remainder are carbon atoms; $R_1$ and $R_2$ are independently a hydrogen atom, a hologen atom, a lower alkyl group, an aryl group, a lower alkoxy group, an aryloxy group, a hydroxymethyl group, an amino group, a mono-lower alkylamino group, a di-lower alkylamino group, a di-lower akloxymethyl group, or $R_1$ and $R_2$ together are a lower alkylenedioxyl group; and Y is an alkoxy group, an aryloxy group, an alkylthio group, an arylthio group, an alkylsulfonyl group, an arylsulfonyl group, and a mono-alkylamino group.

As used throughout this specification and claims, the term "lower alkyl", when taken alone or in combination, denotes a straight-chain or branched-chain saturated hydrocarbon group containing 1 to 8 carbon atoms, for example, methyl, ethyl, propyl, isopropyl, butyl, tert-butyl, neopentyl, pentyl, heptyl, and t-octyl. The term "lower alkoxy" when taken alone or in combination, denotes a lower alkyl ether group in which the lower alkyl group is as defined earlier; for example,methoxyl, ehthoxyl, propoxy and pentoxy. The term "halogen" denotes the four halogens, bromine, chlorine, fluorine and iodine. The term "aryl" denotes phenyl or phenyl bearing one or more halogens, trifluoromethyl, lower alkyl, lower alkoxy, nitro, amino, lower alkylamino and/or di-lower alkylamino substituents. The term "aryloxy" denotes an aryl ether group in which the aryl group is as defined earlier, for example, phenoxy. The term "lower alkylenedioxy" denotes an alkylene diether group containing from 1 to 8 carbon atoms such as methylenedioxy, ethylenedioxy and propylene-dioxy. The term "lower alkylene" denotes a hydrocarbon group containing 2 to 5 carbon atoms such as ethylene, propylene, butylene and pentylene. The term "aralkyl" denotes a lower alkyl group in which one or more of the hydrogen atoms have been replaced by an aryl group (e.g. benzyl). The term "cycloalkyl" denotes a cyclic hydrocarbon group containing from 3 to 6 carbon atoms. Examples of aryl-lower alkoxy groups are benzyloxy,1-phenylethyloxy. Examples of mono-lower alkylamino groups are methylamino, ethylamino, propylamino, isopropylamino, butylamino and pentylamino and t-octylamino. Examples of di-lower alkylamino groups and dimethylamino, diethylamino, ethylmethylamino and dipropylamino.

The N-methylphenyl formimidate, the N-methylpyridyl formimidate and the N-methyldiazyl formimidate derivatives are known and can be prepared by known procedures. For example, ethyl or methyl N-(2-methylphenyl) formimidate is prepared by condensation of the O-toluidine with an excess of triethylorthoformate or trimethylorthoformate in the presence of a catalytic amount of an acid. This acid can be hydrogen chloride, phosphoric acid, benzene sulfonic acid, trifluorosulforic acid or any organic or inorganic compound which can furnish acidic proton. This condensation reaction can be carried out in the presence or absence of an organic solvent. In the most preferred case, the condensation is effected by a catalytic amount of phosphoric acid, benzene sulfuric acid or trifluorosulfonic acid in the absence of any solvent.

Suitable alkali metal amides are alkylamides of the formula

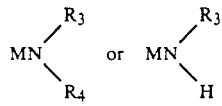

or alkali metal hexamethyldisilazide, having the formula

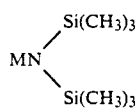

wherein M is potassium, sodium or lithium cation; and $R_3$ and $R_4$ are independently a lower alkyl group, a cycloalkyl group, or $R_3$ and $R_4$ together are a lower alkylene group. These amides generally have a pKa of about 30 or higher and generally the more basic alkylamides are preferred. Lithium alkylamides are less preferred reactants as resultant yields are lower.

The alkylamides are known and can be prepared by known procedures. There is disclosed in my pending application Ser. No. 507,168, filed June 23, 1983, incorporated by reference herein, a method of preparing potassium dialkylamides by reaction of a dispersion of molten potassium with the appropriate dialkylamine and an electron acceptor, for example, α-methylstyrene, whose carbanion is more basic than the amine, in excess dialkylamine or a solvent for the electron acceptor that is more basic than the electron acceptor carbanion. Monoalkylamides can also be prepared by this method, using monoalkylamines in place of dialkylamines. The preferred solvents for this reaction are the alkylamine or butyl ether, but hydrocarbons, such as alkanes, cycloalkanes and aromatic hydrocarbons such as benzene and toluene can be used. In addition to the alkylamide, the resultant reaction mixture will contain solvent and by-product cumene. It is a feature of this invention that the reaction mixture can be used directly in the indole forming reaction, without the need to separate the potassium alkylamide.

The indoles obtained according to this invention have the general formula

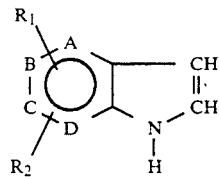

wherein A, B, C, D, $R_1$ and $R_2$ are as defined above in relation to the formimidate reactant.

While, in general, substituents represented by $R_1$ and $R_2$ are unaffected by the metallation reaction, in certain cases, such as substituent hydroxyl or aldehyde groups, they may be affected. Such groups can be protected according to usual organic synthesis practice by conversion to an unaffected group for the synthesis reaction and reconversion of the group in the indole product. For example, hydroxyl group can be protected by conversion to an ether group and aldehyde by conversion to a dialkoxymethyl group.

The reaction is believed to proceed simultaneously through the metallation and cyclization step, as exemplified by the following equations representing the believed mechanism of a preferred preparation of indole from potassium diethylamide and methyl-N-(2-methyl-6-ethylphenyl)formimidate.

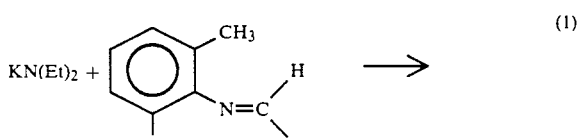

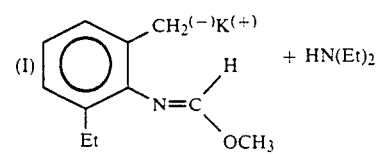

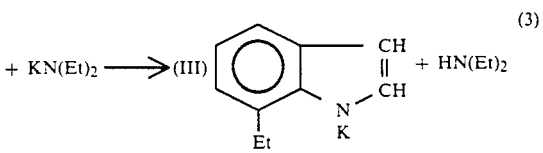

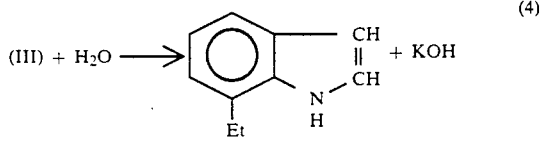

The metallated formimidate (I) spontaneously cyclizes to intermediate (II) and by-product $KOCH_3$. Since the allyllic proton of intermediate (II), α to the benzene ring, is more acidic than any proton of the starting formimidate, the intermediate (II) is more reactive than the formimidate and thus reacts as rapidly as it is formed with alkylamide to yield the potassium salt of indole (III). The potassium salt is readily converted to indole by treatment with water [reaction (4)]; the alkoxide product of reaction 2 is also hydrolized to KOH and alcohol. The indole is separated from the reaction mixture by conventional methods, suitably by vacuum distillation after removal of alcohol, followed by extraction with hexane and drying by sodium sulfate.

The reaction conditions are not narrowly critical, but it is an advantage that the reaction proceeds at ordinary ambient temperatures. The reaction can be carried out at a temperature between about −30° C. and 150° C., at ordinary or superatmospheric pressures.

Reaction solvents compatible with the amide are suitable for use, such as for example, the amine corresponding to the amide, trialkylamines, butyl ether or hydrocarbons, such as alkanes, cycloalkanes and aromatic hydrocarbons such as benzene and toluene.

The following examples are illustrative of the invention and the now preferred embodiments thereof.

EXAMPLE 1

Dry di-n-butylamine (774 g.), 10 drops of monochlorobenzene (as dispersing agent) and 33.7 g. potassium metal were charged to a 2-liter three-necked flask under nitrogen equipped with a dropping funnel, a reflux condenser, a thermometer, a mechanical stirrer and a nitrogen inlet and a bubbler. The potassium was dispersed with high speed agitation at 70° C. for 5 minutes. α-methylstyrene (52.4 g.) was then added dropwise, at such a rate that the exothermic reaction maintained the temperature at about 75° C. Upon the completion of addition of α-methylstyrene, stirring was continued for one hour. THrough this period, a milky suspension developed. The reaction mixture containing potassium di-n-butylamide was then cooled to 20° C.

Ethyl N-(2-methyl-6-ethylphenyl)formimidate (65.9 g.) in 50 ml. of di-n-butylamine was slowly added, over about 5 minutes, to the potassium di-n-butylamide reaction mixture at 20° C. The metallation and cyclization reactions were substantially instantaneous under these reaction conditions. The transient appearance of a deep red color characteristic of benzyl anion was developed and discharged immediately upon contact of ethyl N-(2-methyl-6-ethylphenyl)formimidate with the potassium amide reaction mixture near the neck of the reactor. All solids dissolved resulting in a light brownish solution. Stirring was continued for another half hour. Then 150 ml. of ethyl alcohol were added to destroy the excess amide and unreacted metal and also to convert potassium indole salt to indole. After the removal of the excess alcohol at reflux temperature (159° C.) through a distillating column packed with Fenske packing materials, a brown oily material separated and settled at the bottom of the flask. The top amine layer was decanted off. The brown oily layer was dissolved in 300 ml. of hexane, then washed with 500 ml. water which was extracted with two 300 ml. portions of hexane. The combined hexane extracts were dried over $Na_2SO_4$ and filtered. Evaporation of volatile components furnished 39.8 g. of 7-ethylindole (80.0 percent yield) of over 98.5 percent purity.

EXAMPLE 2

To a 500 ml. three-necked Morton flask equipped with a 60 ml. dropping funnel containing 7.94 g. (8.72 ml.) of α-methylstyrene in 20 ml. of di-n-propylamine, a reflux condensor, a thermometer and a mechanical stirrer with a nitrogen inlet and a bubbler were charged 140 ml. of dry di-n-propylamine, 2 drops monochlorobenzene and 5.00 g. potassium metal under nitrogen.

The potassium was dispersed with high speed agitation at 70° C. for 5 minutes. The α-methylstyrene [7.94 g. (8.72 ml.) in 20 ml. of di-n-propylamine] was then added dropwise at such a rate that the temperature was maintained at around 75° C. Upon the completion of addition of the α-methylstyrene, stirring was continued for two hours. The reaction mixture containing potassium di-n-propylamide was then cooled to 20° C. with an ice-bath, and 9.78 g. of ethyl N-(2-methyl-6-ethylphenyl)formimidate were added slowly (5 minutes) through the dropping funnel together with 20 ml. of the amine used for dilution. After stirring for thirty minutes, 30 ml. of ethyl alcohol were added to destroy the excess amide and unreacted metal. The solution was transferred to a 500 ml. round bottom flask. After all volatile components had been removed by vacuum, the residue was treated with 100 ml. water, and extracted with two 100 ml. portions of ether. The combined ether layers were dried over $MgSO_4$ and filtered. Evaporation of ether in warm water bath yielded 7.80 g. of crude product in the form of dark brown liquid. Vacuum distillation furnished 5.53 g. (74%) 7-ethylindole of 97% purity.

EXAMPLE 3

To a 500 ml. three-necked Morton flask equipped with a 60 ml. dropping funnel, a reflux condensor, a thermometer and a mechanical stirrer were charged 140 ml. of dry dicyclohexylamine, 2 drops monochlorobenzene and 5.00 g. potassium metal under nitrogen.

The potassium was dispersed with high speed agitation at 70° C. for 5 minutes. The α-methylstyrene [7.94 g. (8.72 ml.) in 20 ml. of dicyclohexylamine] was then added dropwise at such a rate that the temperature was maintained at around 75° C. Upon the completion of addition of the α-methylstyrene, stirring was continued for two hours. The reaction mixture containing potassium dicyclohexylamide was then cooled to 20°60 C. with an ice-bath, and 9.78 g. of ethyl N-(2-methyl-6-ethylphenyl)formimidate added slowly (5 minutes) through the dropping funnel together with 20 ml. of the amine used for dilution. After stirring for thirty minutes, 30 ml. of ethyl alcohol were added to destroy the excess amide and unreacted metal. The solution was transferred to a 500 ml. round bottom flask. After the alcohol and most of the dicyclohexylamine solvent had been removed by vacuum, the residue was dissolved in 100 ml. diethyl ether and washed with 150 ml. 2N HC1acid. The precipitate of dicyclohexylamine salt was filtered off. The aqueous layer was separated and extracted with two 100 ml. portions of ether. The combined ether layers were dried over $MgSO_4$ and filtered. Evaporation of ether followed by vacuum distillation yielded 5.11 g. (69 percent) of 7-ethylindole having a boiling point of 75° C./0.10 mm.

EXAMPLE 4

To a 500 ml. three-necked Morton flask equipped with a 60 ml. dropping funnel, a reflux condensor, a thermometer and a mechanical stirrer with a nitrogen inlet and a bubbler were charged 140 ml. of dry di-n-propylamine, 2 drops monochlorobenzene and 5.00 g. potassium metal under nitrogen.

The potassium was dispersed with high speed agitation at 70° C. for 5 minutes. The α-methylstyrene [7.94 g. (8.72 ml.) in 20 ml. of di-n-propylamine] was then added dropwise at such a rate that the temperature was maintained at around 75° C. Upon the completion of addition of the α-methylstyrene, stirring was continued for two hours. The reaction mixture was then cooled to 20° C. with ice-bath, and 9.07 g. methyl N-(2-methyl-6-ethylphenyl)formimidate was added slowly (5 minutes) through the dropping funnel together with 20 ml. of the amine used for dilution. After stirring for half an hour, 30 ml. of ethyl alcohol were added to destroy the excess amide and unreacted metal. The solution was transferred to a 500 ml. round bottom flask. After all volatile components had been removed by vacuum, the residue was treated with water, and extracted with two 100 ml. portions of ether. The combined ether layers were dried over $MgSO_4$ and filtered. Evaporation of ether followed by vacuum distillation gave 5.30 g. (72 percent) of 7-ethylindole as a colorless liquid.

EXAMPLE 5

To a 500 ml. three-necked Morton flask equipped with a 50 ml. dropping funnel containing 11.33 g. (12.45 ml.) of α-methylstyrene in 20 ml. of di-n-butylamine, a reflux condensor, a thermometer and a mechanical stirrer were charged 150 ml. of dry di-n-butylamine, 2 drops mono-chlorobenzene and 5.46 g. of potassium-sodium alloy containing 56 percent of potassium under nitrogen.

The alloy was dispersed with high speed agitation at 70° C. for 5 minutes. The α-methylstyrene was then added dropwise at such a rate that the temperature was maintained at around 75° C. Upon the completion of addition of the α-methylstyrene, stirring was continued for one and one-half hours. The reaction mixture was then cooled to 25° C. with an ice-bath, and 13.97 g. of ethyl N-(2-methyl-6-ethylphenyl) formimidate were added slowly (5 minutes) through the dropping funnel together with 20 ml. of the amine used for dilution. After stirring for thirty minutes, 30 ml. of ethyl alcohol were added to destroy the excess amide and unreacted metal. The solution was transferred to a 500 ml. flack. After all volatile components had been removed by vacuum, the residue was treated with 100 ml. water which was extracted with two 100 ml. portions of ether. The combined ether layers were dried over MgSO4 and filtered. Evaporation of ether followed by vacuum distillation gave 7.40 g. (70 percent) of 7-ethylindole.

EXAMPLE 6

To a 500 ml. three-necked Morton flask equipped with a 60 ml. dropping funnel containing 7.94 g. (8.82 ml.) of α-methylstyrene in a mixture of triethylamine (12.8 ml.) and diethylamine (7.2 ml.), a reflux condensor, a thermometer and a mechanical stirrer were charged 83 ml. of dry triethylamine, 47 ml. of diethylamine along with 2 drops monochlorobenzene and 500 g. potassium metal under nitrogen.

The potassium was dispersed with high speed agitation at 68° C. for 5 minutes. The α-methylstyrene was then added dropwise. Upon the completion of addition of the α-methylstyrene, stirring was continued for an hour. The reaction mixture was then cooled to 10° C. with dry ice-acetone bath and 9.78 g. of ethyl N-(2-methyl-6-ethylphenyl)formimidate were added slowly (5 minutes). After stirring for thirty minutes at 10°-17° C. and thirty minutes at room temperature, 25 ml. of ethyl alcohol were added to destroy the excess amide and unreacted metal. The solution was transferred to a 500 ml. round bottom flask. After a similar workup, the yield of 7-ethylindole was 82%.

EXAMPLE 7

To a 500 ml. three-necked Morton flask equipped with a 60 ml. dropping funnel containing 7.94 g. (8.72 ml.) of α-methylstyrene in 20 ml. of triethylamine, a reflux condensor, a thermometer and a mechanical stirrer were charged 83 ml. of dry triethylamine, 36.0 g. (47.0 ml.) of hexamethyldisilizane to reactor along with 2 drops monochlorobenzene and 5.99 g. potassium under nitrogen.

The potassium was dispersed with high speed agitation at 70° C. for 5 minutes. The α-methylstyrene was then added dropwise. Upon the completion of addition of the α-methylstyrene, stirring was continued for 15 minutes, the 9.78 g. of ethyl N-(2-methyl-6-ethylphenyl)formimidate were added slowly (5 minutes) to the reaction mixture containing potassium hexamethyldisilazide at the same temperature (70° C.). After stirring at this temperature for one hour and cooling to room temperature, 25 ml. of ethyl alcohol were added to destroy the excess amide and unreacted metal. The solution was transferred to a 500 ml. round bottle flask. After a similar workup, the yield of 7-ethylindole was 82%.

We claim:
1. A method of preparing indole and derivatives thereof of the formula

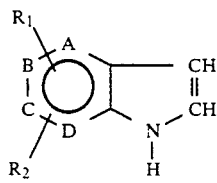

wherein not more than two of A, B, C, and D are nitrogen atoms and the remainder are carbon atoms; wherein $R_1$ and $R_2$ are independently a hydrogen atom, a halogen atom, a lower alkyl group, a lower alkoxy group, a hydroxymethyl group, an amino group, a mono-lower alkylamino group, a di-lower alkylamino group, a phenyl group or substituted phenyl group having a halogen, trifluoromethyl, lower alkyl, lower alkoxy, nitro, amino, lower alkylamino, or di-lower alkylamino substitutent, a phenoxy group or substituted phenoxy group having a halogen, trifluoromethyl, lower alkyl, lower alkoxy, nitro, amino, lower alkylamino, or di-lower alkylamino substituent, or a di-lower alkoxymethyl group, or $R_1$ and $R_2$ together are a lower alkylenedioxy group on adjacent carbon atoms, which comprises the step of contacting an alkali metal amide of the formula

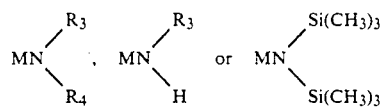

wherein M is an alkali metal and $R_3$ and $R_4$ are independently a lower alkyl group, a cycloalkyl group or $R_3$ and $R_4$ are a lower alkylene group;
with a formimidate derivative of the formula

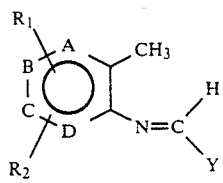

wherein A, B, C, D, $R_1$ and $R_2$ are as defined above and Y is an alkoxy group, an aryloxy group, an alkylthio group, an arylthio group, an alkylsulfonyl group, or an arylsulfonyl group, at a temperature between about −30° C. and 150° C., thereby forming an alkali metal salt of said indole or derivative thereof,
and converting the salt to indole or a derivative thereof by reaction with water or alcohol.

2. A method according to claim 1 in which the amide is a potassium alkylamide.

3. A method according to claim 1 in which Y is methoxy.

4. A method according to claim 1 in which Y is ethoxy.

5. A method according to claim 1 in which the alkali metal amide is provided in a reaction mixture resulting from the reaction of a molten potassium dispersion with an alkylamine and an electron acceptor whose carbanion is more basic than the amine in excess amine or a solvent for the electron acceptor that is more basic than the electron acceptor carbanion.

6. A method according to claim 5 in which the amide is potassium di-n-ethylamide and Y is methoxy or ethoxy.

7. A method of preparing 7-ethylindole which comprises the step of contacting ethyl N-(2-methyl-6-ethylphenyl) formimidate or methyl N-(2-methyl-6-ethylphenyl) formimidate with an alkali metal amide of the formula

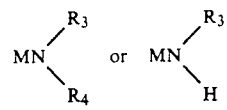

wherein M is an alkali metal and $R_3$ and $R_4$ are independently a lower alkyl group, a cycloalkyl group or $R_3$ and $R_4$ together are a lower alkylene group at a temperature between about $-30°$ C. and $150°$ C., thereby forming an alkali metal salt of 7-ethylindole, and converting the salt to 7-ethylindole by reaction with water or alcohol.

8. A method according to claim 7 in which the amide is a potassium amide.

* * * * *